United States Patent [19]

Poncy et al.

[11] 4,002,276
[45] Jan. 11, 1977

[54] SURGICAL GLOVE DONNING SYSTEM

[76] Inventors: Mark P. Poncy; George W. Poncy; Richard P. Poncy, all of 3670 E. Indus. Way, Riviera Beach, Fla. 33404

[22] Filed: Aug. 1, 1975

[21] Appl. No.: 600,893

[52] U.S. Cl. .................. 223/111; 206/278
[51] Int. Cl.² ........................ A47J 51/06
[58] Field of Search ......... 223/1, 111; 2/270, 168; 312/1; 21/2, 83; 141/65; 92/34, 35, 12.1, 12.2; 206/278

[56] References Cited

UNITED STATES PATENTS

| 882,312 | 3/1908 | Hoefftcke | 223/11 |
|---|---|---|---|
| 1,938,685 | 12/1933 | Breuls et al. | 223/111 |
| 1,996,377 | 4/1935 | Hinchen | 223/111 |
| 2,741,410 | 4/1956 | LaViolette | 223/111 |
| 2,842,773 | 7/1958 | Trexler | 2/270 |
| 3,009,164 | 11/1961 | Freif | 2/270 |
| 3,067,001 | 12/1962 | McCollum | 223/111 X |
| 3,103,016 | 9/1963 | Perlman | 2/270 |
| 3,237,821 | 3/1966 | Hayne et al. | 223/111 |
| 3,328,846 | 6/1967 | Boddy | 2/270 X |
| 3,695,493 | 10/1972 | Karr | 223/111 |

Primary Examiner—G. V. Larkin
Attorney, Agent, or Firm—Lane, Aitken, Dunner & Ziems

[57] ABSTRACT

The donning of surgical gloves is facilitated by inflating the surgical glove with the cuff open so that the surgeon may insert his hand into the glove while inflated and then deflating the glove around the surgeon's hand. The glove is mounted in a glove package with the cuff of the elastomeric surgeon's glove stretched around a ring. The ring with the glove so mounted is mounted at the mouth of a tube which telescopes into a larger tube making a sliding air seal with the larger tube. When the smaller tube is withdrawn from the larger tube, the reduced air pressure that results within the chamber defined by the tubes sucks the glove into the chamber and inflates it in the chamber. After the surgeon has inserted his hand into the inflated glove, the inner tube is then reinserted into the outer tube to increase the pressure within the chamber above atmospheric causing the cuff of the glove to explode off the ring on which it is mounted and snap around the surgeon's wrist.

10 Claims, 14 Drawing Figures

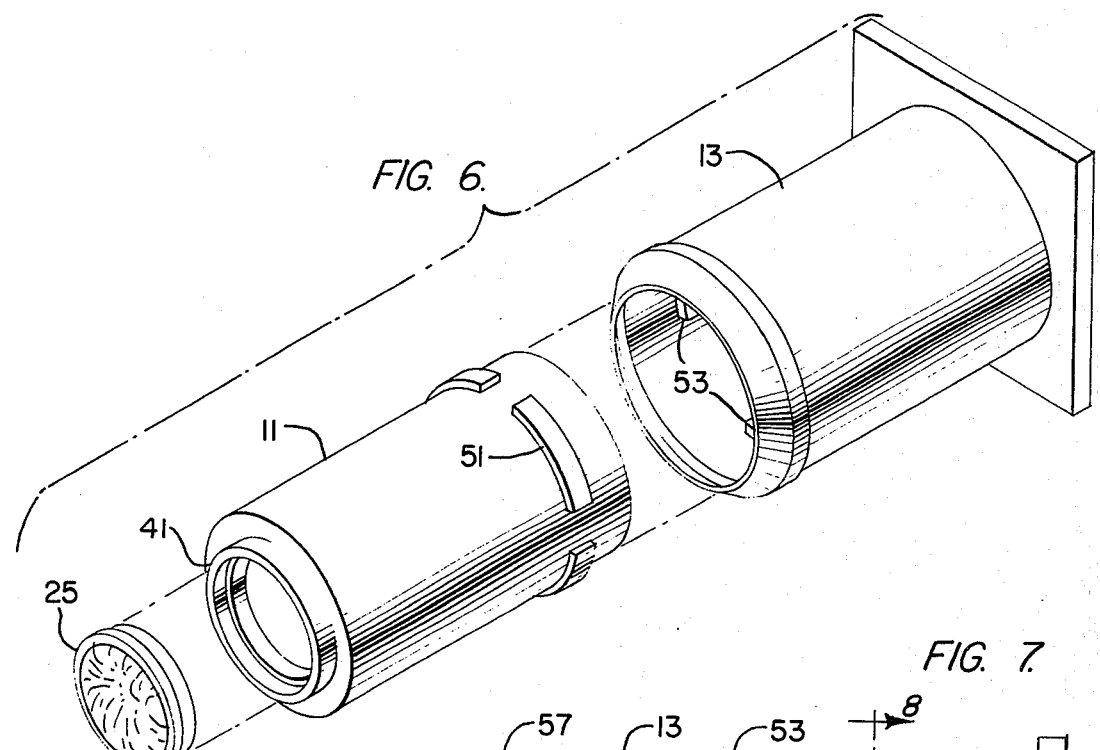
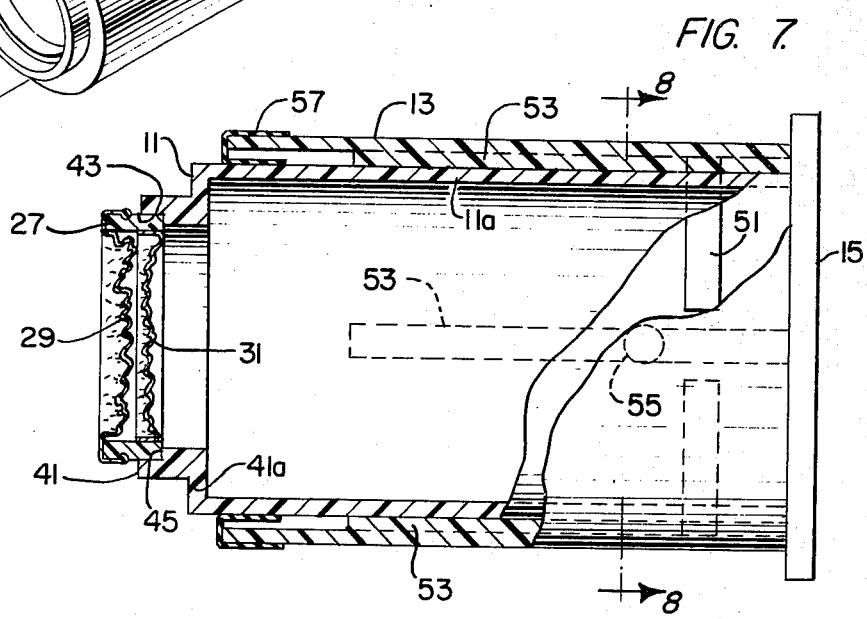
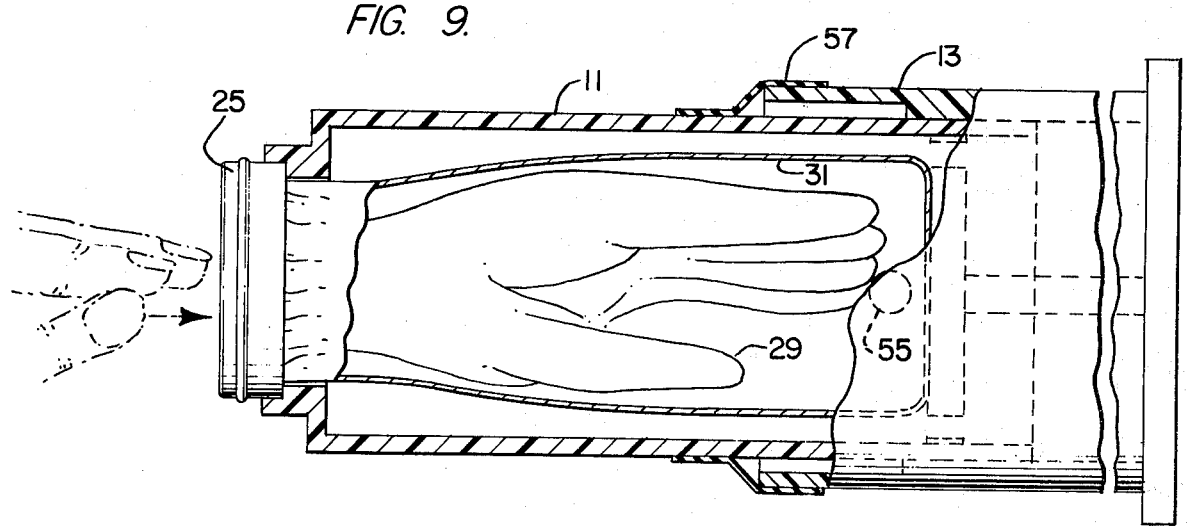

SURGICAL GLOVE DONNING SYSTEM

BACKGROUND OF THE INVENTION

This invention relates to a surgical glove package and a simple apparatus designed for use therewith which greatly facilitates the donning of surgical gloves and eliminates the possibility of accidental contamination of the outer glove surfaces during the procedure of donning the gloves.

The technique now used for donning surgical gloves require that the sealed package containing sterile gloves be carefully opened so that the inner surfaces of the package, and more particularly, the outside surfaces of the gloves contained therein, do not come in contact with any surface. Upon being opened, the gloves are positioned next to each other with the large part of the cuff portions of the gloves being turned on themselves or inside out. An assistant grasps one glove by the folded cuff portion so as to touch only that surface when the glove is donned. The touched surface will thus correspond only to the glove's inner surface. After removing the glove from the package, the assistant grasps the cuff portion of the glove with the fingers of both hands and stretches the opening as much as possible in order to enlarge the cuff opening. The glove is then held in a somewhat vertical position in order to present the glove opening to the surgeon's hand. Care must be taken to make sure that the drooping glove fingers do not touch any surface other than the adjacent outer glove surfaces. The surgeon then vigorously thrusts his hand into the enlarged glove opening in an attempt to gain full entry into the fingers of the glove. The assistant must maintain a firm grip on the glove cuff portion in order to provide the resistance to the thrust necessary for the surgeon's hand to gain access to the fingertips of the glove. At the precise moment the surgeon's hand reaches the fingertips, the assistant must release hold of the glove to permit the cuff portion to snap tightly around the surgeon's wrist. The same procedure is followed for donning the second glove.

Obviously this procedure is fraught with accidental contamination possibilities, especially during times of distress and urgency as may exist when torn gloves have to be replaced during an operation. In addition, this technique requires assistance of a second person with the necessary skill. Moreover, because of the difficulty in fully inserting the hand into the glove, the inner surfaces of the glove must be heavily powdered to lubricate the glove surface relative to the surgeon's hand. The powdering operation normally results in powder getting on the external surfaces of the glove. As a result, the surgeon must use sterile wipes to cleanse the glove surfaces of powder because the presence of powder particles in the surgical wound would aggravate internal organs and tissue and would adversely affect healing following surgery.

In the instances where the user of latex gloves does not have any assistance, care must be taken to avoid touching the outer surface to avoid contamination. This is difficult to do since the wearer must also stretch the glove enough to provide access with one hand while inserting the other.

SUMMARY OF THE INVENTION

The glove package and the apparatus of this invention make it possible for the surgeon to don the surgical gloves quickly and easily without assistance and without any powder appearing on the outside of the glove. The system of the present invention comprises a glove inflating apparatus which generates in a chamber a low pressure. The surgical glove package of the present invention is positioned over an opening to the chamber. The low pressure in the chamber greatly inflates the glove within the chamber so that it resembles a swollen cow udder in appearance. With the glove thus inflated, the enlarged opening of the glove is presented to the surgeon's hand, which is easily accommodated right to the fingertip ends of the glove without any difficulty. When the hand has been fully inserted into the glove, a slight twist of the surgeon's hand restores the pressure in the chamber to atmospheric pressure and permits the surgical glove to instantly snap back to conform tightly around and encase the surgeon's hand. At this time, the surgeon pushes the gloved hand forward within the chamber. This slight forward movement increases the air pressure within the chamber, which serves to release the cuff portion from the glove package. Upon release of the glove from the package, the surgeon then simply withdraws his gloved hand from the apparatus.

The procedure may then be repeated to don the second glove since the glove package containing the second glove can easily be positioned on the apparatus across the opening with the remaining ungloved hand. Alternatively, however, separate glove inflating apparatus for each hand may be employed with the packaged glove being inflated on each apparatus prior to the donning of the gloves.

The glove inflating apparatus comprises a pair of telescoping tubes with a sliding air seal provided between the tubes and with the outer tube closed at one end. The glove in a specially designed package is placed over the opening of the inner tube. When the inner tube is withdrawn from the outer tube, the low pressure produced in the chamber within the tubes inflates the glove.

The sliding air seal between the telescoping tubes is provided by means of a cylindrical elastomeric band, such as a wide rubber band, having one side fixed in a stretched condition to the end of the outer tube so that the other side of the band flexes against the outer cylindrical surface of the inner tube.

The present invention thus makes possible a simple and easy technique for the surgeon to don the surgical gloves without assistance.

In addition, the present invention provides a simple, inexpensive apparatus for inflating a flexible device such as a surgeon's glove and a simple inexpensive, but very effective air seal between telescoping cylinders.

The present invention also provides a convenient surgeon's glove package designed to be inflated on the apparatus and serving as a convenient means for shipping and storing the sterile gloves.

Should the glove to be donned be defective for reason as having a pinhole, the glove will not inflate. Thus, the existance of the pinhole will become immediately apparent.

Further objects and advantages of the present invention will become readily apparent as the following detailed description of the invention unfolds when taken in conjunction with the drawings identified below.

BRIEF DESCRIPTION OF THE DRAWINGS

FIG. 6 is an exploded view of the glove inflating apparatus of the invention with a glove package to be inflated;

FIG. 7 is a partial sectional view in elevation of the glove inflating apparatus with the glove package mounted in position on the apparatus to be inflated;

FIG. 9 is a partial sectional view in elevation of the glove inflating apparatus showing a glove inflated in the chamber thereof;

DESCRIPTION OF THE PREFERRED EMBODIMENTS

Figure 1:
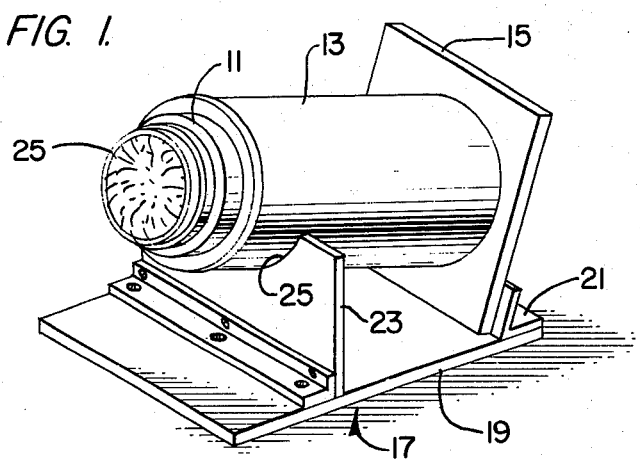
FIG. 1 is a perspective view of the apparatus of the invention with the surgical glove package mounted on the apparatus of the invention ready to be inflated by the apparatus.

As shown in FIG. 1, the glove inflating apparatus comprises a pair of telescoping tubes 11 and 13. The outer tube 13 has a plate 15 fixed to the bottom thereof closing off the end of the tube 13 with an airtight seal. The tubes 11 and 13 may be made of any suitable rigid material, but a transparent plastic material such as an acrylic is preferred. The assembly of the telescoping tubes 11 and 13 and the plate 15, which comprise the glove inflating apparatus, are supported on a stand 17. The bottom edge of the plate 15 rests on a support plate 19 of the stand 17 against a bracket 21 which is secured to the support plate 19. The front end of the tube 13 rests on a vertically extending wall 23 secured to the horizontal supporting plate 19. The wall 23 is provided with a recess 25 shaped to fit around the outer cylindrical surface of the tube 13 and the tube 13 is cradled in this recess. The wall 23 is proportioned relative to the dimensions of the plate 15 so that the axes of the tubes 11 and 13 are inclined at an angle of about 15° or 20° from horizontal with the front end of the tubes 11 and 13 resting on the wall 23 positioned higher than the back ends of the tubes 11 and 13 at which the plate 15 is located. This means that the plate 15 will be inclined from the vertical and the upstanding wall of the bracket 21 is inclined with respect to vertical at the same angle so that the back of the plate 15 rests flush against the wall of the bracket 21.

Figure 2:
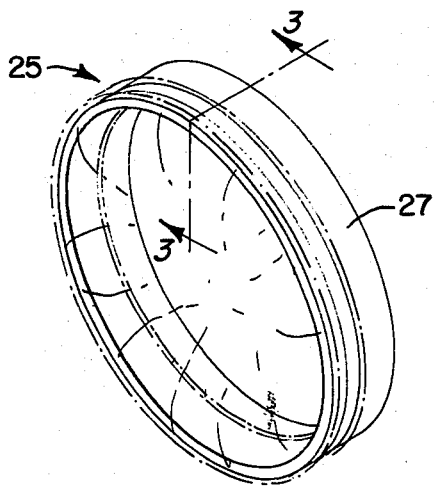
FIG. 2 is a perspective view of one embodiment of the surgical glove package of the invention.
Figure 3:
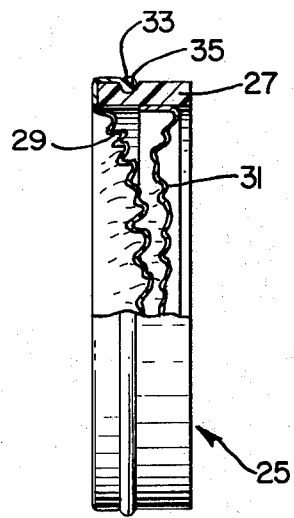
FIG. 3 is a partial sectional view taken along the line 3—3 of FIG. 2 illustrating the surgical glove package in elevation.

A package containing a surgical glove is shown mounted on the front end of the inner telescoping tube 11 in FIG. 1 and is designated by the reference numeral 25. The glove package 25, as better shown in FIGS. 2 and 3, comprises a ring 27, which may be made of paperboard or may be molded from a rigid plastic such as styrene or high density polyethylene. A conventional surgical glove 29, which is made of a thin, impervious, elastomeric material is removably mounted on the ring 27 together with a thin, flexible, impervious, transparent sleeve 31 covering the outer surface of the glove 29. The outside walls of the sleeve 31 at one end thereof are sealed to the ring 27. The other end of the sleeve 31 is preferably sealed closed so that the sleeve 31 forms a bag completely enclosing the outer surfaces of the glove. As shown in FIGS. 2 and 3, the outer surfaces of the mouth of the sleeve 31 are sealed to the inner cylindrical wall of the ring 27. However, the sleeve 31 may be secured to the ring by sealing the inner sufaces of the mouth of the sleeve to the outer surface of the ring 27. The sleeve 31 may be made from very thin, flexible, plastic film.

The embodiment of the package shown in FIGS. 2 and 3 is designed for gloves provided with a bead at the end of the cuff portion of the surgical glove. The cuff of the surgical glove is stretched around the end wall of the ring and the bead of the glove designated by the reference number 33 fits in a circular groove 35 extending around the cylindrical wall of the ring 27. Since the cuff of the glove 29 is stretched around the end of the ring 27, it fits tightly against the ring 27 so that the sleeve 31 sealed around the ring 27 completely encloses the outer surface of the gloove 29 and protects the sterility thereof.

The gloove 29 and the sleeve 31 are folded up within the cylinder defined by the walls of the ring 27 so as to provide a compact, convenient package for storage and transportation. The package is sealed with appropriate outer wrapping, which is removed before the package is placed on the glove inflating apparatus, and the gloves thus packaged are provided with suitable identification "right" and "left." The contents of the sealed package are sterilized with ethylene oxide gas in the conventional manner as well known in the art.

Figure 4:
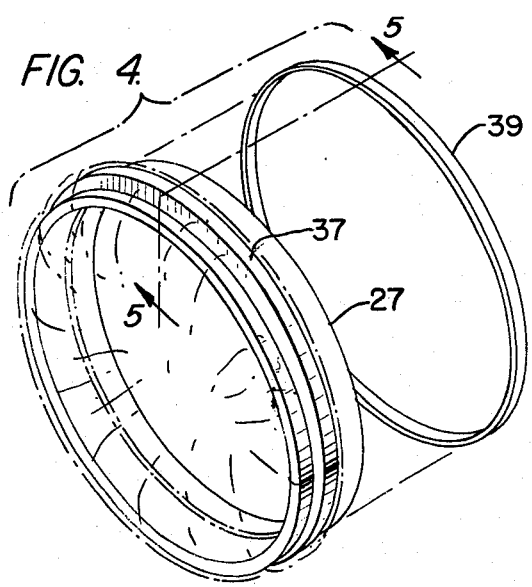
FIG. 4 is an exploded perspective view of another embodiment of the surgical glove package of the invention.
Figure 5:
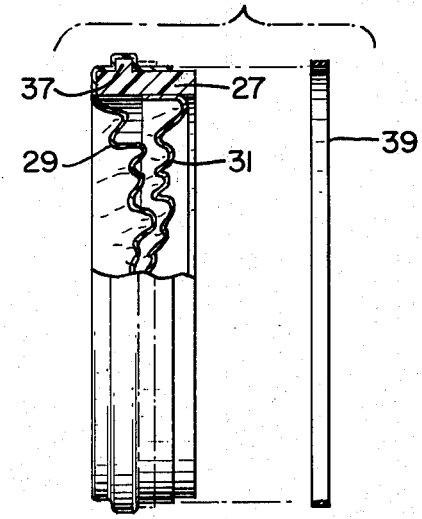
FIG. 5 is a partial sectional view taken along the line 5—5 of FIG. 4 showing the glove package of FIG. 4 in elevation.

The alternative embodiment of the ring package illustrated in FIGS. 4 and 5 is designed for use with gloves which do not have a bead at the cuff end of the glove. In this embodiment, the ring is provided with a ridge 37 extending around the outer suface of the ring 27 and the sleeve of the gloove 29 is stretched around the end of the ring and over the ridge 37. An elastic band 39, such as a conventional rubber band, is provided to secure the cuff end of the glove to the ring 27. The rubber band is positioned around the cuff portion of the glove against the shoulder defined by the ring 37 on the opposite side thereof from the end of the ring 27 around which the cuff portion of the glove 29 is stretched.

As best shown in FIGS. 6 and 7, the front end or mouth of the inner tube 11 has a section 41 reduced in diameter at the mouth of the tube 11 for mounting the glove package 25. The section 41 is provided with a stepped inner cylindrical wall surface having a larger diameter inner wall section 43 adjacent the mouth thereof to define a shoulder 45 facing the mouth of the tube 11. The structure of the reduced opening may be conveniently provided by cementing to the end of a plastic tube section, which forms the main body 11a of the tube 11, a ring to form the radially extending wall 41a. Then two tubular rings, one fitting within the other, may be cemented to the radially extending wall to form the reduced diameter section 41 with the shoulder 45 being provided by the inner tubular ring being axially shorter than the outer tubular ring. The outer cylindrical surface of the ring 27 is designed to fit sufficiently tightly within the cylindrical wall section 43 against the shoulder 45 to form an air seal. An air tight seal may be affected by means of a rubber gasket, which is cemented to the outside of tube 11 and extends approximately ¼ inch beyond the inner wall section 43 in order to flex around the outer rim of ring 27. The diameter of the reduced end section 41 as well as that of the ring package 45 need only be large enough to permit entry of the surgeon's hand, which upon initial entry into the inner tube 11 will be held in the somewhat closed normal position for donning a glove as shown in FIG. 9. The reduction in the diameter at the mouth of the tube 11 minimizes the amount that the cuff of the glove has to be stretched while at the same time permitting a larger diameter interior of the tube 11 to permit flexing of the surgeon's hand to facilitate donning of the glove once inside the tube 11.

Figure 8:
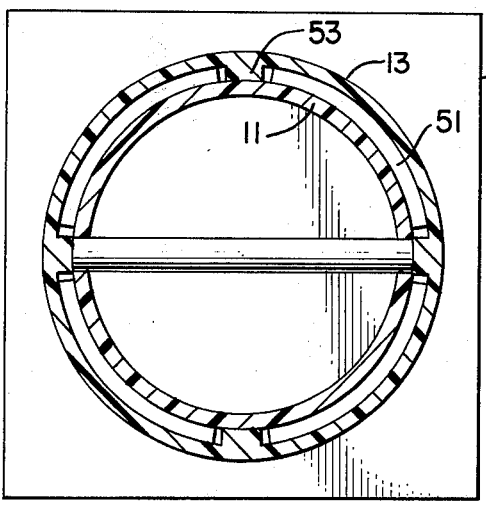
FIG. 8 is a sectional view taken along the line 8—8 of FIG. 7.

Near the back end of the tube 11 on the outer cylindrical wall thereof are cemented arcuate segments 51 arranged in a circular configuration around the tube 11 as shown in FIGS. 7 and 8. The segments 51 make a sliding fit with the inner cylindrical wall surface of the outer tube 13. The gaps between the segments 51 define grooves in which axially extending guide bars 53 are positioned. The guide bars 53 are cemented to the inner cylindrical wall of the outer tube 13 and make a sliding fit with the outer cylindrical wall of the inner tube 11. Thus, a clearance is provided between the outer cylindrical surface of the outer tube 13 to accommodate the segments 51 and the guide bars 53.

A round rod 55 is mounted in the inner tube 11 extending across the diameter thereof near the back end thereof. This tube facilitates manipulation of the inner tube relative to the outer tube in the operation of using the apparatus to free the surgical glove from the package after the user has inserted his hand into the glove and also aids in maintaining a desired orientation of the inner tube relative to the glove and surgeon's hand during this operation as is described below.

Figure 10:
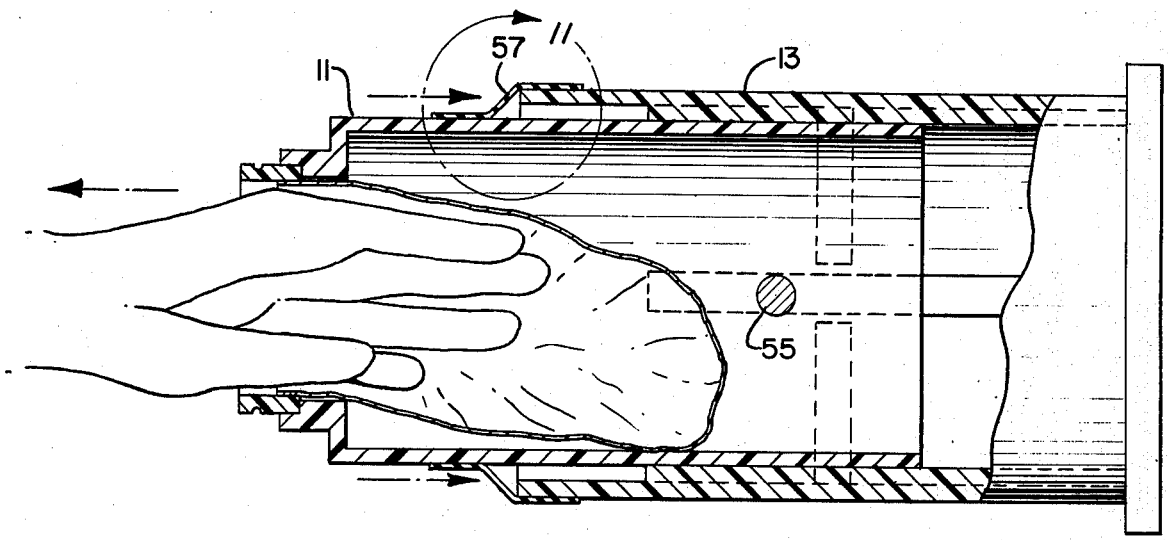
FIG. 10 is a partial view in elevation of the glove inflating apparatus of the invention showing a point of operation of the apparatus after the glove has encased the surgeon's hand.
Figure 11:
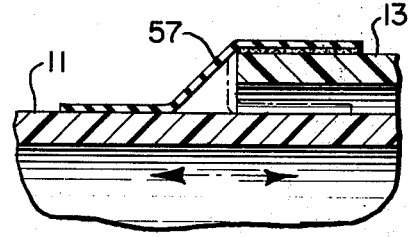
FIG. 11 is an enlarged sectional view showing the sliding air seal of the inflating apparatus.

As best shown in FIGS. 7, 8, 10 and 11, a wide circular elastomeric band 57 is cemented to the outer cylindrical surface of the tube 13 at the front end thereof so that part of the elastomeric band 57 extends out beyond the front end of the tube 13. The band 57 is mounted on the front end of the tube 13 in a stretched position so that the distal end of the rubber band 57 extending out beyond the front end of the tube 13 is reduced in diameter and engages the outer cylindrical surface of the tube 11 thus providing a sliding air seal between the tubes 11 and 13 at the mouth or front end of the tube 13. As shown in FIG. 7, when the tube 11 is all the way in the tube 13, the elastomeric band 57 will wrap around the front edge of the tube 13 and engage the tube 11 with the surface of the elastomeric band which is normally the outer surface thereof. When the inner tube 11 is pulled out from the outer tube 13, as shown in FIG. 9, the elastomeric band 57 will unfold and the inner surface of the rubber band 57 will engage the outer cylindrical surface of the tube 11 as shown in FIGS. 9, 10 and 11 while maintaining the air seal around the tube 11 at the mouth of the tube 13.

In operation, the assembly of the tubes 11, 13 and base plate 15 are placed on the stand 17 as shown in FIG. 1 and the ring package containing the surgeon's glove is positioned in the mouth of the tube 11 against the shoulder 45 as shown in FIGS. 1 and 7. The tube 11 is then withdrawn from the tube 13 thus causing the pressure inside the tube 13 to be reduced as a result of the sliding air seal between the tubes 11 and 13 and the air seal between the ring 27 and the mouth of the tube 11. As a result of this reduced pressure, air will flow into the mouth of the tube 11 through the ring 27 to suck the glove 29 and sleeve 31 into the chamber defined within the tubes 11 and 13 and inflate the sleeve 31 and the glove 29 as shown in FIG. 9. The inner tube 11 is withdrawn far enough for the segments 51 to be past the end of the guide bars 53 and the inner tube 11 is rotated to bring a portion of the segments 51 in axial alignment with the guide bars and thus lock the inner tube 11 in the withdrawn position. The reduced air pressure generated within the tubes 11 and 13 acting through the inflated and stretched glove will exert a force on the inner tube to tend to draw it back into the tube 13 and hold the segments 51 against the guide bars 53. With the glove inflated in this manner, the surgeon can then easily insert his hand through the ring 27 and the mouth of the tube 11 and fully into the inflated surgeon's glove 29. Because the glove 29 will be fully inflated to a size larger than the surgeons'hand, the surgeon's hand goes fully into the glove very easily. The surgeon then continues to thrust his hand forward until he grasps the bar 55 with his fingers thus positioning his hand in the glove relative to the tube 11 at a desired orientation. The surgeon then rotates the tube 11 with respect to the tube 13 back to its original angular position in which the guide bars 53 register with the gaps between the segments 51, at which time the reduced pressure within the tube 13 will pull the tube 11 back toward the fully inserted position along with the hand of the surgeon encased in the glove 29. The surgeon at this time will press the inner tube forward holding onto the bar 55 until the cuff of the glove explodes off the ring and onto his wrist. The cuff does, in fact, explode off the ring and around the wrist as he pushes the inner tube forward because this action will cause the pressure inside the tube 13 to exceed the atmospheric pressure and thus exert pressure between the cuff of the glove 29 and the ring 27 where the cuff is mounted on the ring. The air pressure will cause the cuff of the glove to release from the ring onto the surgeon's wrist with a pronounced popping sound. If the bar 55 were not present, then the rotation of the inner tube 11 relative to the outer tube 13 would have to be done by the surgeon flexing his hand to an open position to engage the tube 11 and the tube 11 would have to be made small enough to permit this to be done. This in turn might interfere with the normal flexing operation of the hand as the hand is being inserted into the glove particularly for persons with large hands. Thus, the bar 55 enables the inner tube 11 to be made large enough, five inches in diameter, to accommodate the largest handed user of the apparatus.

In addition, the bar 55 provides another very important function. When the surgeon inserts his hand into the tube 11 and grabs the bar 55, he then determines a fixed orientation of the glove 29 relative to the tube 11 and the ring 27 during the time that the tube 11 is being reinserted into the tube 13. If the bar 55 were not there, then when the inner tube 11 is rotated back to the position in which the guides 53 register between the segments 51, the reduced pressure inside the tube 13 might draw the tube 11 into the tube 13 faster than the gloved hand moves into the tube 13 and thus cause an unwrapping of the sleeve of the glove about the wrist of the surgeon and preventing effective release of the sleeve from the ring 27. On the other hand, the surgeon might move his hand in faster or further into the tube 13 than the tube 11 is withdrawn back into the tube 13 and thus cause the cuff of the glove to bind around the front edge of the ring 27 and prevent it from being exploded off during this operation. The grasping of the bar 55 by the surgeon's gloved hand maintains the gloved hand in a fixed position with respect to the inner tube 11 and thus enables the increased pressure inside the tube 13 to effectively explode the cuff of the glove off the ring 27 and onto the surgeon's hand. After the cuff has been released from the ring and snaps around the suregon's wrist, the surgeon then withdraws his gloved hand from the tube 11 and ring 27 as shown in FIG. 10.

Figure 12:
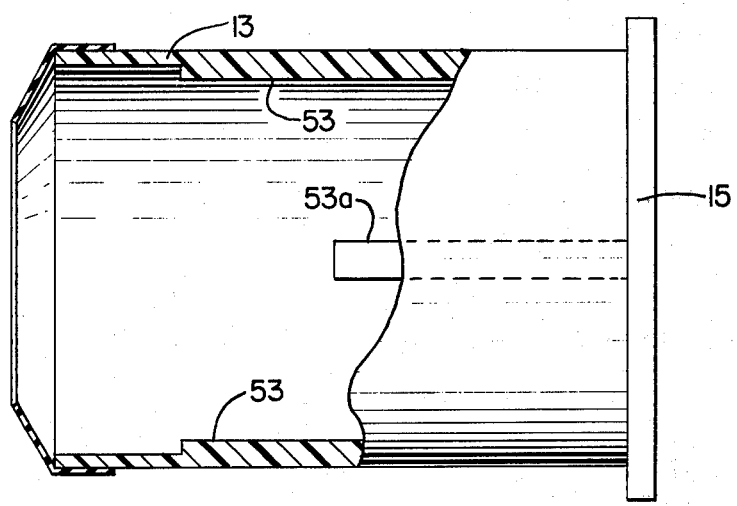
FIG. 12 is a partial sectional view in elevation of just the outer portion of an alternative embodiment of the glove inflating apparatus according to the present invention.
Figure 13:
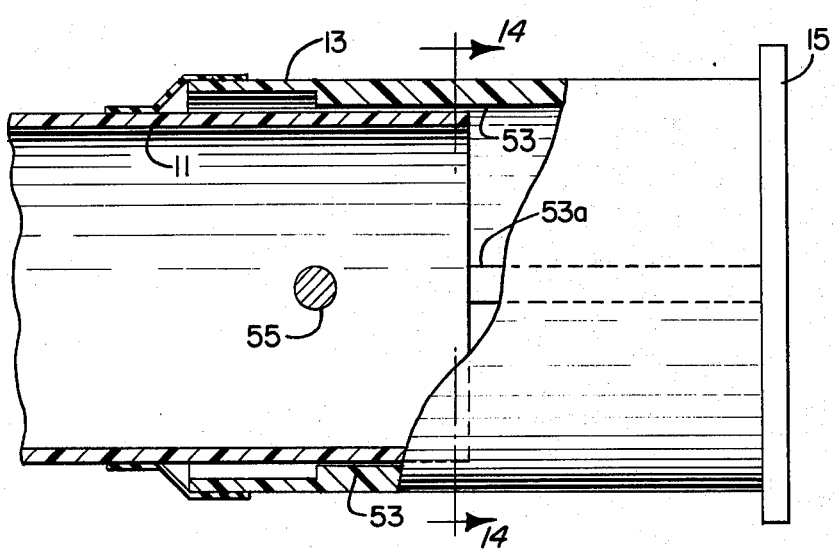
FIG. 13 is a partial sectional view in elevation of the entire glove inflating apparatus embodiment of FIG. 12 illustrating a point of operation thereof.
Figure 14:
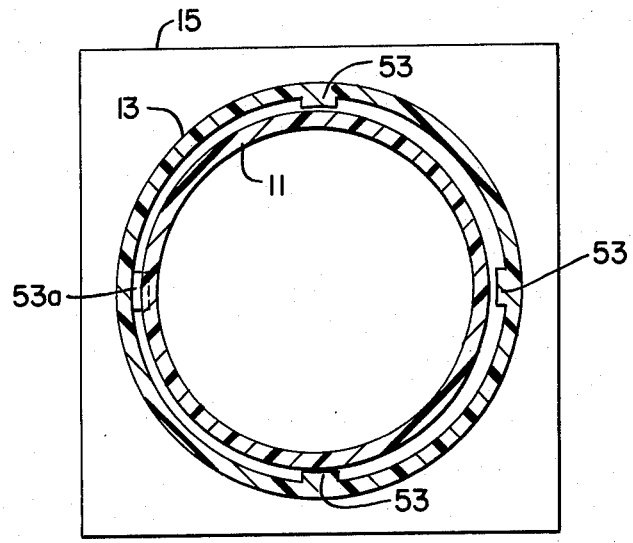
FIG. 14 is a sectional view taken along the line 14—14 of FIG. 13.

In the embodiment of the glove inflating apparatus illustrated in FIGS. 12–14, the arcuate segments 51 have been eliminated and a different system is employed for retaining the inner tube 11 in the withdrawn or extended position after the glove has been inflated. In this embodiment, one of the guide bars 53, designated 53a, is made shorter in axial length than the other guide bars 53 so that the front end of this guide bar terminates about midway in the tube 13. Since the tube 13 preferably is about 10 inches in length, the guide bar 53 will be about 5 inches long with the rear end thereof terminating at the plate 15. The other guide bars 53 are made about seven inches in axial length with the front ends terminating about two inches nearer to the mouth of the tube 13 than the guide bar 53a. The radial thickness of the guide bar 53a is made greater than that of the other guide bars and in the preferred embodiment is ⅛ inch thick. The guide bar on the opposite side from the guide bar 53a is made about 1/16 inch thick in this embodiment and the other two guide bars are each made about 3/32 inch thickness. The thickness of the guide bars is chosen so that a loose or sloppy sliding fit is provided between the guide bars and the outer cylindrical surface of the tube 11. Preferably about 1/16 inch of play is provided between the tube 11 and the guide bars 53 and 53a. This play is achieved by making the sum of the thicknesses through the guide bars on opposite sides from each other equal to about 3/16 of an inch.

The guide bar 53a is given a distinctive color such as red so that it is clearly visible through the clear plastic material of the tubes 11 and 13. The other three guide bars 53 are made of the same clear plastic material as the tubes 11 and 13.

In this embodiment, the glove is inflated just as described above with respect to the embodiment shown in FIGS. 6–8. However, after the tube 11 has been withdrawn, the back tube 11 is retained in the extended or withdrawn position by slightly cocking the tube so that the back end of the tube 11 lodges against the front end of the guide bar 53a as shown in FIGS. 13 and 14. This cocking of the inner tube is permitted by 1/16 inch play between the guide bars and the inner tube 11. With the inner tube cocked and the back end thereof lodged against the front end of the guide bar 53a, the reduced pressure within the tubes 11 and 13 acting through the inflated glove will apply force to the inner tube 11 to hold the back end of the tube 11 against the front end of the guide bar 53a. In this manner, the inner tube 11 is maintained in its extended or withdrawn position with the glove inflated ready for insertion of the surgeon's hand. After the surgeon inserts his hand, he merely grasps the bar 55 and uncocks the inner tube by moving it to one side to disengage it from the guide bar 53a so that the tube 11 may be reinserted back into he tube 13 as described above with respect to the embodiments of FIGS. 6–8.

The above described system of the present invention makes it possible for the surgeon to very quickly and easily don sterile surgical gloves without danger of contamination and without the need for assistance of a second person. Moreover, this easy and effective donning of the gloves is achieved by means of a very simple apparatus and convenient glove package.

The above description is of preferred embodiments of the invention and many modifications may be made thereto without departing from the spirit and scope of the invention which is defined in the appended claims.

We claim:

1. A method of donning a glove comprising mounting said glove on a ring by stretching the cuff portion of said glove around the end edge of said ring to open the cuff portion of said glove for entry of the hand, then inflating said glove, inserting the hand into said glove while inflated, then deflating said glove around said hand and releasing the cuff portion of said glove from said ring by exerting air pressure between said cuff portion and said ring to explode said cuff portion off of said ring.

2. A system for facilitating the donning of a glove comprising mounting means for mounting the glove with the cuff portion of said glove open to receive a hand, inflating means for inflating said glove while said glove is mounted on said mounting means, said inflating means comprising means defining a chamber for generating a low pressure within said chamber, said mounting means including means for positioning said glove in an opening to said chamber in such a manner that when the pressure in said chamber is reduced, said glove is sucked into said chamber and inflated within said chamber, said inflating means comprising a pair of telescoping tubes defining said chamber within said tubes with means providing a sliding air seal between said tubes with one end of one of said tubes being closed and the opposite end of the other of said tubes defining said opening to said chamber.

3. A glove donning system as recited in claim 2, wherein said air seal between said tubes is provided by an elastomeric band having one edge thereof fixed in a stretched condition to the outer one of said tubes with the opposite edge thereof engaging the outer surface of the inner one of said tubes.

4. A system for facilitating the donning of a glove comprising mounting means for mounting the glove with the cuff portion of said glove open to receive a hand, inflating means for inflating said glove while said glove is mounted on said mounting means, and means to release said glove from said mounting means after said glove has been inflated and the hand as been inserted into the inflated glove, said releasing means comprising means to increase the air pressure between the cuff portion of said glove and said mounting means to greater than the pressure around said cuff portion to force said glove from said mounting means.

5. A system for facilitating the donning of a glove comprising mounting means for mounting the glove with the cuff portion of said glove open to receive a hand, and inflating means for inflating said glove while said glove is mounted on said mounting means, said mounting means comprising a ring, the cuff portion of said glove being stretched around the edge of said ring to hold the cuff portion of said glove in an open position, said ring comprising packaging means for packaging said glove separate from said inflating means.

6. An inflating apparatus comprising first and second telescoping tubes with a sliding air seal defined therebetween, the end of said first tube being closed and the opposite end of said second tube defining mounting means for mounting and holding an inflatable device in a position such that when said second tube is withdrawn from said first tube, said inflatable device is sucked into the cavity defined by said tubes and inflated within said cavity.

7. An inflating apparatus as recited in claim 6, wherein said air seal between said tubes is provided by an elastomeric band having one edge thereof fixed in a stretched condition to the outer one of said tubes with the opposite edge theron engaging the outer surface of the inner one of said tubes.

8. In a system having a sliding air seal between a tube and a cylinder telescoping within said tube, the improvement wherein said air seal comprises an elastomeric band having one edge fixed to said tube in a stretched condition with the opposite edge of said elastomeric band engaging the outer surface of said cylinder.

9. A method of donning a glove by means of a low pressure chamber defined by inflating apparatus comprising mounting said glove on a ring while separate from said inflating apparatus by stretching the cuff portion of said glove around one axial end edge of said ring with the outside surface of said glove in contact with said ring to open the cuff portion of said glove for entry of the hand, placing said ring over an opening to said chamber with the other axial end of said ring in contact with the opening of said chamber, reducing the pressure in said chamber to inflate said glove, inserting the hand into said glove, deflating said glove on said hand, and releasing said cuff portion from said ring after said glove has been deflated on the hand.

10. A system for facilitating the donning of a glove comprising inflating means defining a chamber for generating a low pressure within said chamber and having an opening to said chamber, a ring separate from said inflating means, a glove having the cuff portion thereof stretched around one axial end of said ring with the outside surface of said glove in contact with said ring, the other axial end of said ring being designed to fit with said opening to said chamber to form an air seal therewith, said chamber functioning to inflate said glove in said chamber when the air pressure in said chamber is reduced with the ring positioned on said opening, said inflating means including means to deflate said glove and release said cuff portion from said ring after a hand has been inserted into said glove.

* * * * *